United States Patent [19]
Ura

[11] Patent Number: 5,944,525
[45] Date of Patent: Aug. 31, 1999

[54] DENTAL IMPLANT AND METHOD AND APPARATUS FOR INSTALLING THE SAME

[76] Inventor: Robert S. Ura, 5763 Long Brake Cir., Edina, Minn. 55439

[21] Appl. No.: 09/036,926

[22] Filed: Mar. 9, 1998

Related U.S. Application Data

[60] Provisional application No. 60/040,675, Mar. 11, 1997, and provisional application No. 60/040,941, Mar. 17, 1997.

[51] Int. Cl.[6] .................................................... A61C 8/00
[52] U.S. Cl. .......................................... 433/173; 433/141
[58] Field of Search .................................... 433/141, 173, 433/174

[56] References Cited

U.S. PATENT DOCUMENTS

| | | | |
|---|---|---|---|
| 4,995,810 | 2/1991 | Soderberg | 433/174 |
| 5,062,800 | 11/1991 | Niznick | 433/229 |
| 5,108,288 | 4/1992 | Perry | 433/173 |
| 5,145,371 | 9/1992 | Jorneus | 433/173 |
| 5,199,873 | 4/1993 | Schulte et al. | 433/174 |
| 5,322,443 | 6/1994 | Beaty | 433/141 |
| 5,538,428 | 7/1996 | Staubli | 433/173 |
| 5,582,299 | 12/1996 | Lazzara et al. | 206/63.5 |
| 5,620,323 | 4/1997 | Bressman et al. | 433/174 |
| 5,692,904 | 12/1997 | Beaty et al. | 433/141 |
| 5,702,346 | 12/1997 | Lazzara et al. | 433/173 |
| 5,709,547 | 1/1998 | Lazzara et al. | 433/174 |

*Primary Examiner*—John J. Wilson

[57] ABSTRACT

A dental implant mount and an implant driver assembly in which the driver assembly is moveable between first and second positions to drive the implant and implant mount for installation of the implant and to remove the clamp screw and the implant mount. The invention also relates to a method of installing a dental implant.

24 Claims, 4 Drawing Sheets

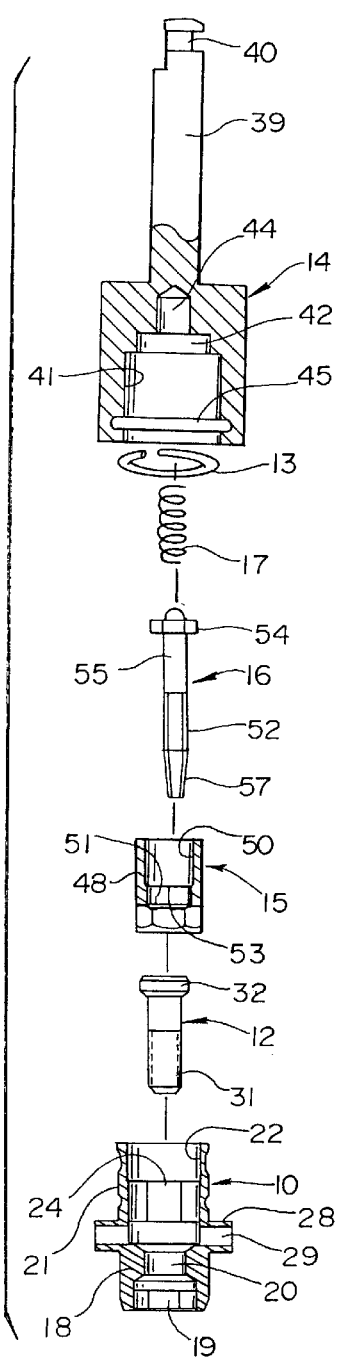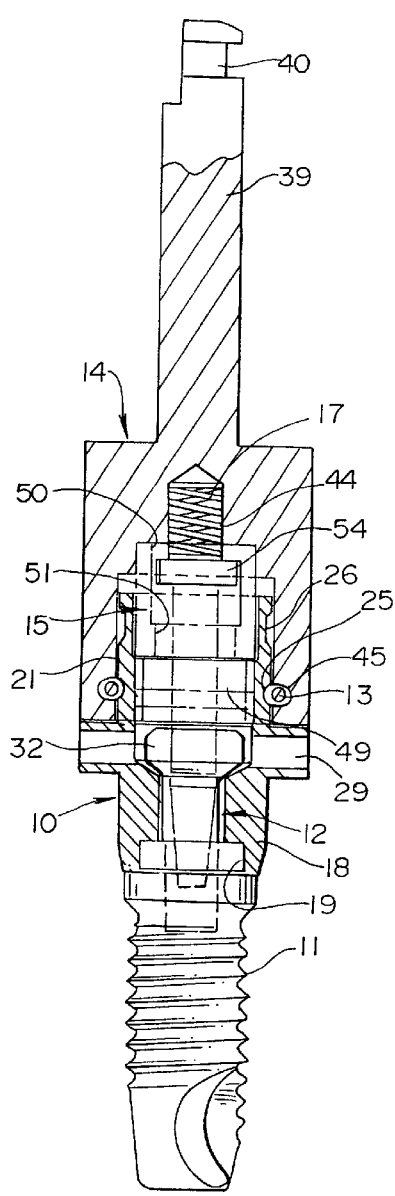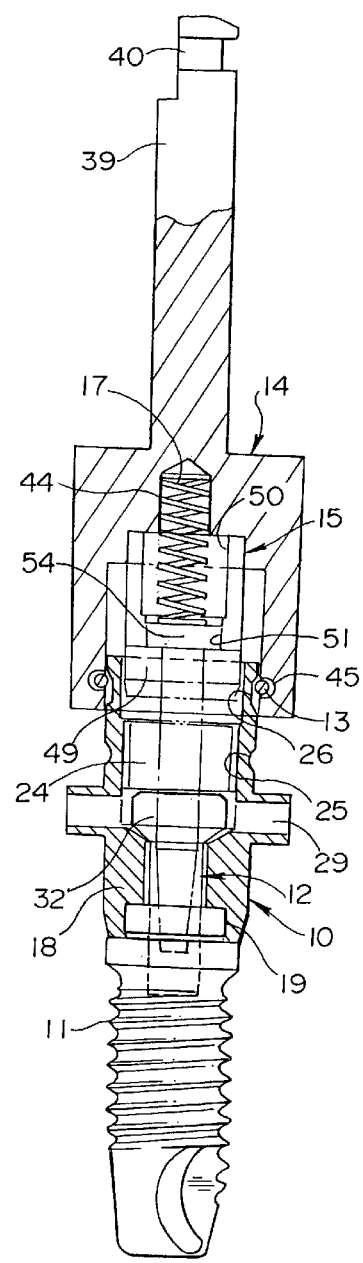

DENTAL IMPLANT AND METHOD AND APPARATUS FOR INSTALLING THE SAME

This application claims the benefit of Provisional Application Ser. No. 60/040,675 filed Mar. 11, 1997 and Provisional Ser. No. 60/040,941 filed Mar. 17, 1997.

BACKGROUND OF THE INVENTION

1. Field of the Invention

The present invention relates generally to the field of dental implants and more specifically to a dental implant, a method and apparatus for installation of a dental implant, an implant mount with an improved counter-torque feature and a method of making the installation device. The dental implant of the present invention preferably functions as a replacement root which is installed into a prepared bone site and anchors a component such as a tooth, a denture or other dental appliance or devices known in the art.

2. Description of the Prior Art

Dental implants of various configurations currently exist in the art. These implants are installed into prepared bone sites and function as a device for anchoring a component such as a tooth or dental appliance in the patient's mouth. Examples of currently available dental implants are shown in U.S. Pat. No. 5,062,800 issued to Niznick, U.S. Pat. No. 5,368,160 issued to Leuschen, et al. and U.S. Pat. No. 5,582,299 issued to Laxnaru. Existing dental implant devices generally include an implant having external threads for installation into a prepared bone site and internal threads at its superior or top end. Such threads are used for connecting an implant mount during the installation process and for connecting a cap screw or a prosthesis or other dental appliance when the installation is complete. During installation, the implant mount is connected with the implant via a threaded clamp screw. The implant mount interfaces with the implant through a hex connection which enables the implant to be rotated via rotation of the implant mount. It is common for the implant to be provided to the attending surgeon in a pre-mounted position with the implant mount connected to the implant by the clamp screw.

Installation of a dental implant in accordance with current procedures can be summarized as follows. After preparation of the bone site, a dental hand piece with placement adaptor connected thereto is positioned onto the implant mount via a hex or other connection. The implant is then positioned in the prepared bone site and installed by rotation of the implant mount and thus the implant in a forward or clockwise direction. The hand piece with placement adaptor is then removed from the implant mount and an open end wrench is positioned onto the hex end of the implant mount. The wrench functions primarily to stabilize the mount and prevent it from falling into the patient's mouth during removal and secondarily to provide a counter-torque to prevent rotation of the implant during removal of the clamp screw. The clamp screw is threadedly retracted with a screw removal tool and the screw and implant mount, along with the wrench and screw removal tool, are removed from the patient's mouth.

Although existing implant devices function acceptably in many ways, several limitations continue to exist. First, several tools, including the hand piece with placement adapter, the screw removal tool and the open end wrench, are necessary for installation of the implant and subsequent removal of the implant mount. Secondly, removal of the implant mount requires the use of two hands and manual removal of the clamp screw. Specifically, removal of the implant mount involves removing the hand piece with placement adaptor from the implant mount and setting it onto a dental tray, positioning the open end wrench onto the implant mount and, while holding it with one hand, using a second hand to retract the clamp screw with the screw removal tool. When sufficiently retracted, the screw removal tool, the open end wrench and the implant mount and clamp screw are removed from the patient's mouth. This multistep implant mount removal is a relatively time consuming process. Thirdly, except for limited retention means between the wrench and the implant mount, the implant mount and the clamp screw are separate, unattached elements which can be dropped into the patient's mouth during removal. When this occurs, additional time must be spent locating the dropped element and subsequently removing the same.

Accordingly, there is a need in the art for an improved dental implant device and an improved method and apparatus for installing the implant and removing the implant mount and clamp screw in a manner which overcomes the limitations in the prior art.

SUMMARY OF THE INVENTION

In contrast to the prior art, the present invention relates to a dental implant mount and assembly and a method and apparatus for installing a dental implant and removing the implant mount while overcoming the limitations of the prior art. Several advantageous features exist: First, the method and apparatus of the present invention reduces and minimizes the number of tools required for implant installation and implant mount removal. Second, the implant installation and implant mount removal are greatly simplified in accordance with the present invention by providing a method and apparatus by which these procedures can be accomplished with a single tool and with fewer manipulative steps. This results in a more time efficient implant installation and implant mount removal process. Third, the clamp screw in the present invention is retracted via the hand piece, thus eliminating manual removal. Fourth, the implant mount and clamp screw are captured by the hand piece adaptor or placement driver, thereby eliminating any possibility that these elements could be dropped into the patient's mouth during removal. The result is a significantly enhanced method and apparatus which overcomes the limitations in the prior art and provides for more time efficient implant installation and implant mount removal. If counter-torque is desired during removal of the implant mount, the present invention also provides an improved means for applying counter-torque.

The structure of the present invention includes an improved implant mount which, in combination with an implant driver assembly, enables the implant to be driven and installed, the clamp screw and implant mount removed, and the clamp screw and implant mount captured, by a single tool. The driver assembly in accordance with the present invention includes a housing having positioning means for selectively positioning the driver assembly between an inferior or first position relative to the mount in which the driver is operatively engaged with the implant mount and operatively disengaged from the clamp screw and a superior or second position relative to the mount in which the driver is operatively disengaged from the implant mount and operatively engaged with the clamp screw. In the preferred embodiment, the driver housing includes detent or other mounting means which are interfaceable with the implant mount to define the above first and second positions. Most preferably, the connection means includes a split ring or other means between corresponding surfaces of the driver assembly and the implant mount.

The implant driver assembly further includes a screw removal insert device which is spring mounted within the driver housing so that the housing and the screw removal insert are moveable relative to one another along a longitudinal axis. Such relative movement is between a disengaged position (corresponding to the above defined first position) in which the driver housing is free to rotate relative to the screw removal insert, and thus the clamp screw, and an engaged position (corresponding to the above defined second position) in which the screw removal insert, and thus the clamp screw, is engaged with a portion of the driver housing for rotation therewith.

The driver assembly can be selectively positioned between a first position for installation of the implant and a second position for removal of the clamp screw and implant mount.

With the above structure, the method in accordance with the present invention generally includes attaching the hand piece with a driver assembly to the implant mount, with the driver housing in its first position. The implant is then positioned in the prepared bone site and installed by forward or clockwise rotation of the driver assembly and thus the implant mount. When installation is complete, the driver housing is moved to its second position and rotated in a reverse or counter-clockwise direction to withdraw the clamp screw. If desired, counter-torque may be provided via an improved counter-torque means. When this withdrawal is complete, the hand tool with driver assembly and captured clamp screw and implant mount are removed from the patient's mouth.

Accordingly, it is an object of the present invention to provide an improved dental implant mount, implant assembly and driver assembly which overcomes the limitations of the prior art.

Another object of the present invention is to provide an improved driver assembly for a dental implant which captures the implant mount and clamp screw and functions to both install the implant and remove the implant mount and clamp screw.

A further object of the present invention is to provide a driver assembly which is selectively movable between a first position in which the driver and implant mount are operatively connected and the driver and screw removal insert disconnected and a second position in which the driver and the clamp screw are operatively connected and the driver and mount disconnected.

A still further object of the present invention is to provide an implant assembly and in particular an implant mount which is usable with the above described driver assembly.

A still further object of the present invention is to provide an implant mount with an improved counter-torque means.

A still further object of the present invention is to provide an improved implant installation method which includes installing the implant and removing the implant mount and associated clamp screw with a single tool.

These and other objects of the present invention will become apparent with reference to the drawings and the description of the preferred embodiment.

DESCRIPTION OF THE DRAWINGS

FIG. 2 is an elevational, exploded side view, with portions broken away and partially in section, showing the implant mount, clamp screw and driver assembly of the invention.

FIG. 4 is a side elevational view, partially in section, showing the driver assembly in a first position relative to the implant mount.

FIG. 5 is a view similar to that of FIG. 4 showing the driver assembly in a second position relative to the implant mount.

DESCRIPTION OF THE PREFERRED EMBODIMENT

Figure 3:
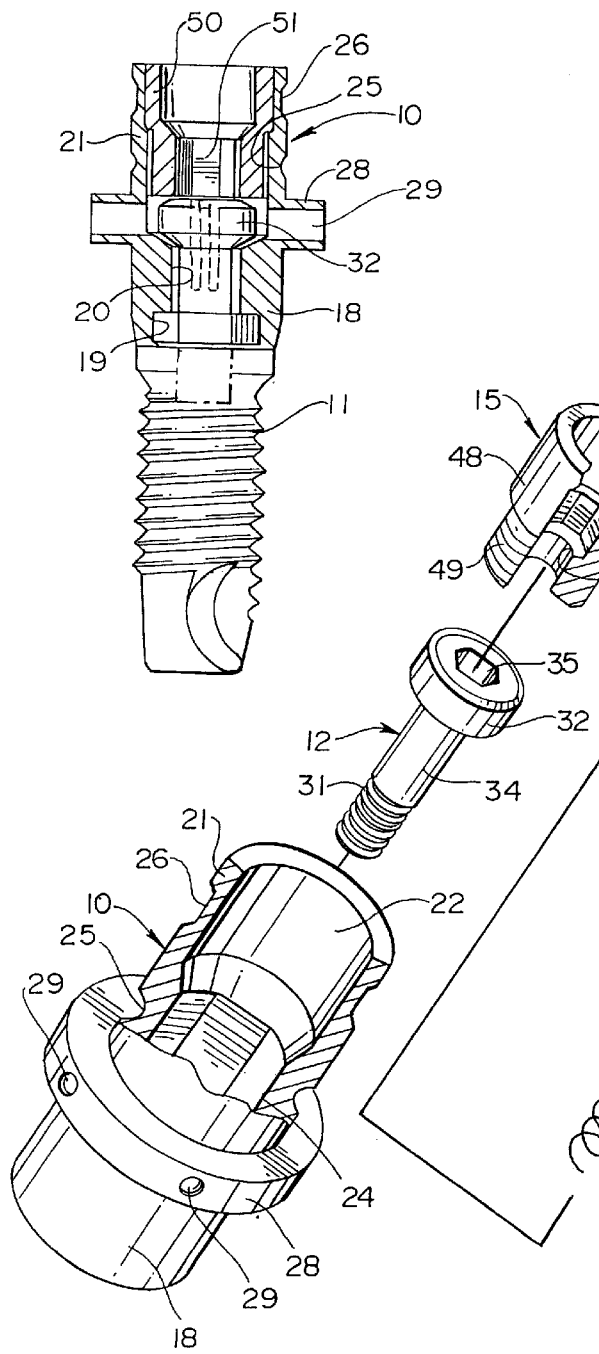
FIG. 3 is an elevational side view, partially in section, of an implant assembly of the present invention.
Figure 1:
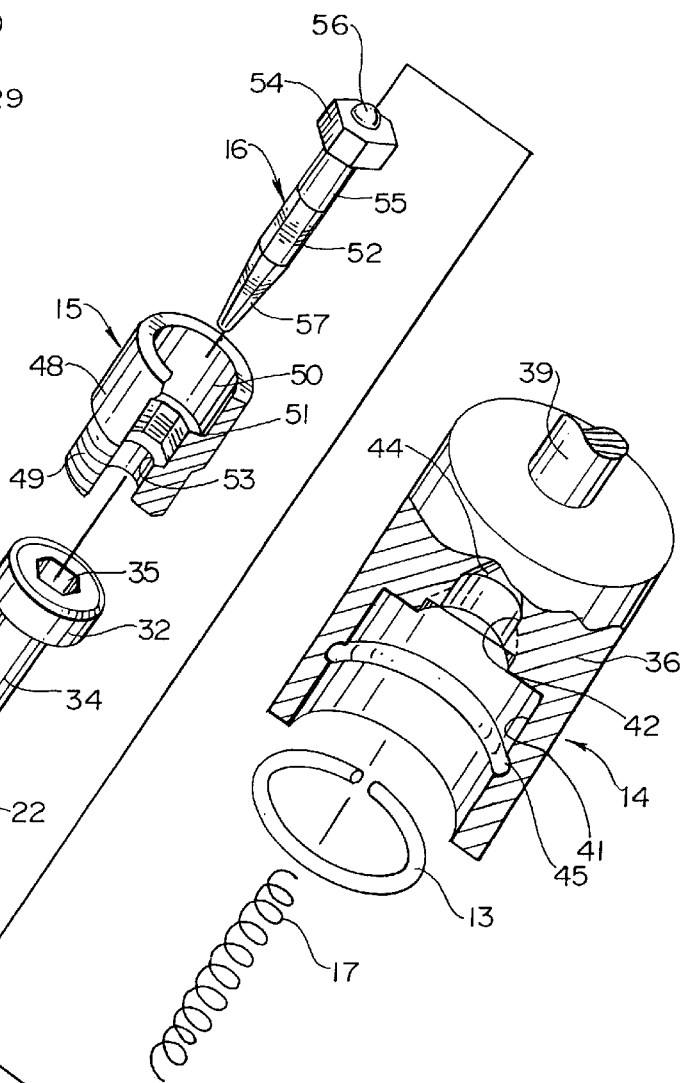
FIG. 1 is an isometric, exploded view, with portions broken away and partially in section, of the implant mount, clamp screw and driver assembly in accordance with the present invention.

Reference is first made to FIGS. 1–5 which illustrate the general structure and operation of the implant mount and driver assembly in accordance with the present invention. The structure of the present invention includes an implant assembly comprised of an implant mount 10, an implant 11 and a clamp screw 12 and a driver assembly comprised of a split ring 13, a driver housing 14, an associated drive member 15, a screw removal insert 16 and a coil spring 17. The spring 17 is positioned between the top of the screw removal insert 16 and an interior portion of the driver housing 14. In the preferred embodiment, the split ring 13 is metal, although it is contemplated that it could be constructed of rubber or other material.

The implant assembly is normally delivered for use in a pre-mounted position as illustrated in FIG. 3 in which the implant mount 10 is mounted to the implant 11 by the clamp screw 12. The implant 11 is a conventional component having a hexagonal or other connecting means at its top end and an internally threaded hole for receiving the clamp screw 12 during installation and a cap screw, prothesis or other appliance (not shown) after installation. As shown in FIGS. 4 and 5, the driver assembly is connectable with the implant mount 10 so that it is selectively positionable between a first position illustrated in FIG. 4 in which the drive member 15 and thus the driver housing 14 are operatively connected with the implant mount 10 and a second position illustrated in FIG. 5 in which the drive member 15 and driver housing 14 are operatively connected with the screw removal insert 16 and thus the clamp screw 12.

More specific illustrations of the various structural components of the present invention and their relationship with one another are now described with reference to FIGS. 6–13. As shown best in FIG. 6, the implant mount 10 includes a lower section 18 having a generally cylindrical exterior configuration. The interior of the section 18 includes a lower connection section 19 in the form of an internal hexagonal or hex configuration and a through opening 20. The internal hexagonal portion 19 is adapted for connection with an external hexagonal configuration of the implant 11 (FIGS.

3–5). The top section of the implant mount 10 includes a sleeve portion 21 having an upper generally cylindrically interior surface 22 and a lower connection surface 24 comprised of an internal hexagonal configuration. As shown, the diametrical dimension of the surface 22 is greater than the largest diametrical dimension of the hexagonal surface 24.

The generally cylindrical exterior surface of the sleeve 21 is provided with first and second positioning means in the form of a first detent or groove 25 and a second detent or groove 26. These grooves 25 and 26 extend circumferencially around the sleeve 21. Positioned between the upper sleeve portion 21 and the lower section 18 is a centrally positioned counter-torque portion 28 having a plurality of radial counter-torque portion 28 having a plurality of radial counter-torque openings 29 about its periphery for applying counter-torque to the implant mount 10 during removal, if desired. An internal surface and shoulder 30 define a cavity to receive the head of the clamp screw 12 and extend between the internal hex configured surface 24 and the opening 20.

Figure 6:
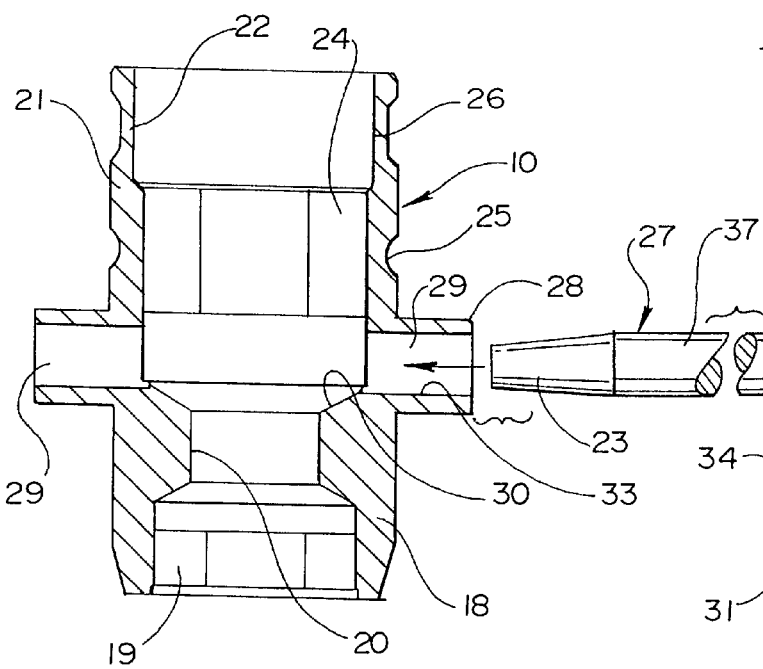
FIG. 6 is a sectional view of the implant mount of the present invention.
Figure 14:
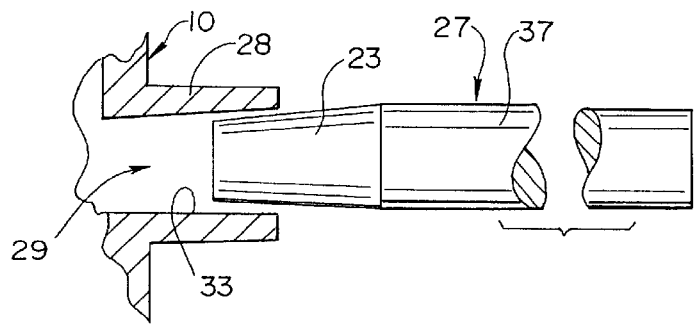
FIG. 14 is a side elevational view, partially in section, of a portion of the implant mount showing one of the counter-torque openings and a counter-torque tool.

As illustrated in FIG. 6, and also in FIG. 14, the counter-torque means of the present invention includes the plurality of radial openings 29. During use, these openings 29 receive a forward end 23 of a counter-torque tool 27. The tool 27 comprises a generally cylindrical handle 37 which can be several inches long for manual manipulation. Preferably the walls 33 of the openings 29 taper slightly inwardly toward the center of the mount 10. Similarly, the outer surface of the end 23 tapers slightly inwardly toward its end so that it substantially matches the taper of the walls 33. This taper helps retain the implant mount relative to the tool 27 when used. The benefits of the counter-torque means can be realized independently of other features of the present invention.

Figure 8:
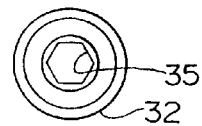
FIG. 8 is a top elevational view of the clamp screw.
Figure 7:
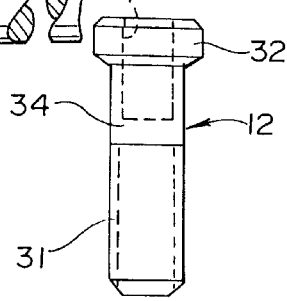
FIG. 7 is a side elevational view of the clamp screw.

As illustrated in FIGS. 7 and 8, the clamp screw 12 includes a lower threaded portion 31, an upper head 32 and a centrally positioned shank 34. A hexagonal interior surface 35 extends from the top surface of the head 32 to a predetermined depth within the shank 34. The threaded portion 31 is designed to be received by the internal threads of the implant 11. The clamp screw 12 functions to secure the implant mount 10 to the implant 11 during installation of the implant.

Figure 9:
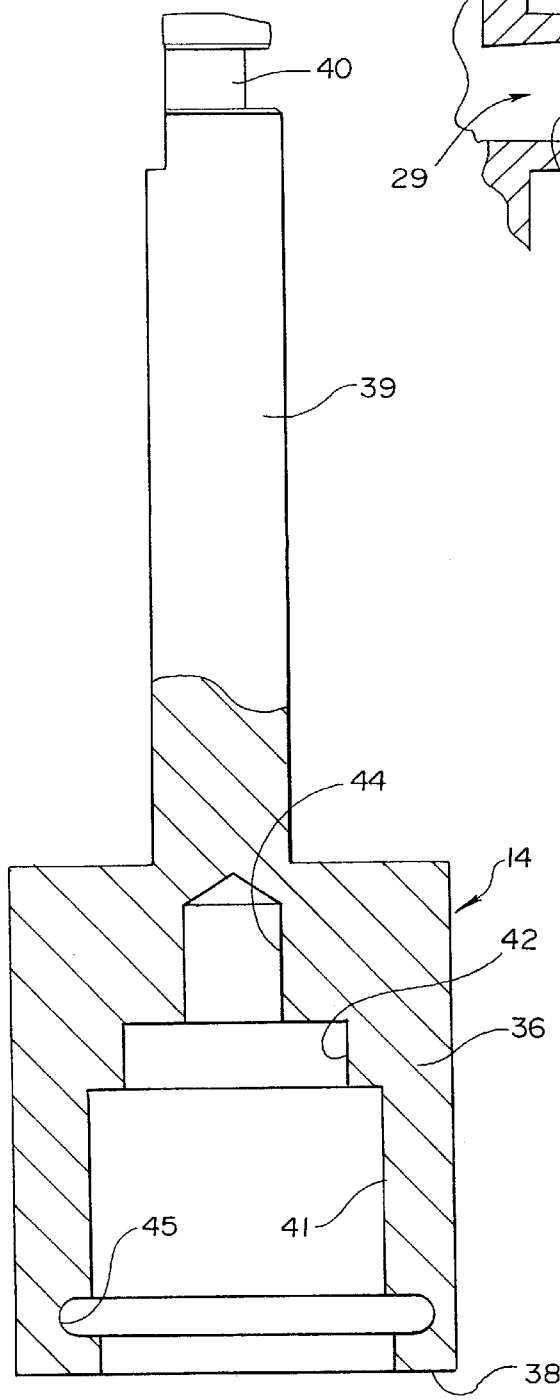
FIG. 9 is a side elevational view, partially in section, of the driver housing.

FIG. 9 illustrates the driver housing 14 which includes a generally cylindrical sleeve section 36 having an open end 38 and an opposite end integrally connected with a hand piece connection shank 39. The distal end of the shank 39 includes a latch attachment mechanism 40 for connecting the shank 39 and thus the entire driver assembly to a dental hand piece in a manner known in the art. The interior of the housing 36 includes a plurality of interior cylindrical surfaces 41, 42 and 44. Positioned at the lower end of the surface 41 is an internal groove or recess 45 for receiving a split ring 13 or similar connecting member. The internal cylindrical surface 42 is adapted for receiving the drive member 16 and the interior surface 44 defines a spring receiving cavity for receiving one end of the coil spring 17 as will be described in greater detail below.

Figure 11:
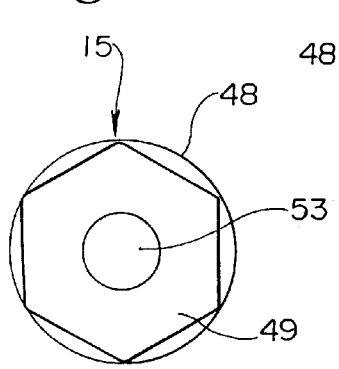
FIG. 11 is a bottom elevational view of the drive member.
Figure 10:
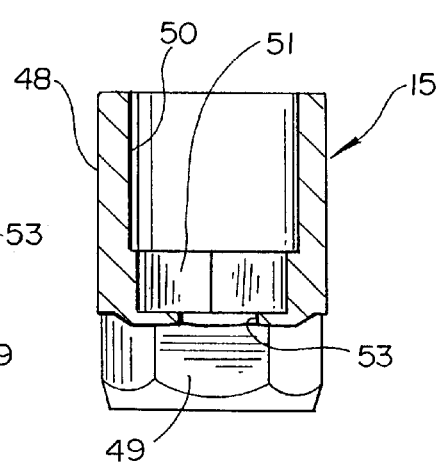
FIG. 10 is a sectional view of the drive member.
Figure 12:
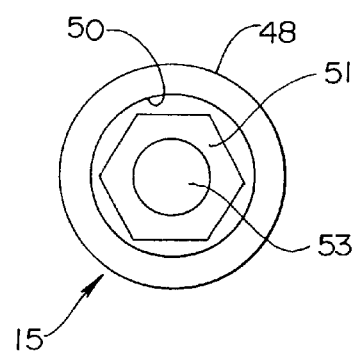
FIG. 12 is a top elevational view of the drive member.

With reference to FIGS. 10, 11 and 12, the drive member 15 is a generally cylindrically shaped member having an outer cylindrical surface 48 at its upper end and an outer hexagonally configured surface 49 at its lower end. The hexagonal lower end 49 is designed for selective insertion into and driving engagement with the internal hexagonal surface 24 of the implant mount 10 (FIG. 6). The interior of the drive member 15 includes an upper interior cylindrical surface 50 and a lower surface 51 of hexagonal configuration designed to receive and operatively engage the hexagonal end of the screw removal insert 16 as will be described in greater detail below. As shown, the inner diametrical dimension of the cylindrical surface 50 is greater than the greatest diametrical dimension of the hexagonal surface 51. This allows free rotational movement of the head 54 of the screw removal insert 16 within the upper portion 50. The outer dimension of the surface 48 approximates the inner dimension of the cylindrical surface 42 of the driver housing 14 and is designed for insertion into the cylindrical opening defined by the surface 42 and laser welded or otherwise rigidly secured thereto. This connection between the drive member 15 and the driver housing 14 is accomplished after appropriate insertion of the coil spring 17 and the screw removal insert 16 as described below.

Figure 13:
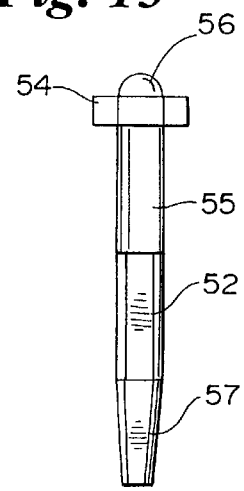
FIG. 13 is a side elevational view of the screw removal insert.

The screw removal insert 16 as shown in FIG. 13 includes a lower portion 52 with an exterior hexagonal configuration, a top head 54 with an exterior hexagonal configuration and a central, cylindrical shank portion 55 between the portion 52 and the head 54. The lower end 57 of the hexagonal portion 52 is beveled as shown to provide a lead-in surface for the portion 52. A raised or dimple portion 56 is provided on top of the head 54 for capturing the coil spring 17 when assembled. The hexagonal portion 52 is designed for insertion into the hexagonal opening 35 in the clamp screw head 34 for operative engagement therewith.

When fully assembled, the driver assembly is capable of selective positioning between a first or inferior position in which the driver assembly is operatively engaged with the implant mount 10 as shown in FIG. 4 and a second or superior position in which the driver assembly is operatively engaged with the screw removal insert 16 and thus the clamp screw 12 as shown in FIG. 5.

To assemble the driver assembly, the screw removal insert 16 is positioned relative to the drive member 15 so that the hexagonal portion 52 and shank 55 (FIG. 13) extend through the opening 53 (FIG. 12) and the head 54 is positioned within the area defined by the cylindrical surface 50 or the hexagonal surface 51. The coil spring 17 is then positioned on top of the head 54 so that it is centered on the raised dimple 56 and the entire assembly is inserted into the driver housing 14 so that the spring 17 is received by the cylindrical spring receiving cavity 44 and the cylindrical upper surface 48 of the drive member 15 is received by the surface 42. The member 15 is then rigidly secured to the housing 14 via laser welding or the like. The driver assembly is now ready for use.

To use the driver assembly of the present invention, the assembly is connected to a dental hand piece (not shown) and the open end 38 of the housing 14 is positioned over the top end of the implant mount 10 so that the sleeve portion 21 of the implant mount 10 is extends into the cylindrical area defined by the surface 41 of the housing 14. This connection is normally made while the implant assembly comprising the mount 10 and the connected implant 11 are in a package or under sterile conditions. During connection between the driver assembly and the mount 10, the housing 14 is preferably moved to its first or inferior position illustrated in FIG. 4 in which the retaining or split ring 13 engages the lower positioning recess 25. In this position, the hexagonal configured end 49 of the member 15 is positioned in operative engagement with the interior hexagonal configured portion 24 of the mount 10 and the hexagonal portion 52 of the screw removal insert 16 is positioned within the hex opening 35 of the clamp screw 12 and is biased into this position by the spring 17. Because of engagement between the bottom end of the insert 16 and the bottom of hexagonal opening 35 and the relative position of the housing 14, and thus the member 15, the head 54 of the insert 16 is in the portion of the member 15 defined by the surface 50. Thus, in this first or inferior position, the drive member 15 is operatively disengaged from the screw removal insert 16 and thus the clamp screw 12. To facilitate this relationship, the length of the insert 16 from the bottom of the head 54 to the bottom of the lower end 57 must be sufficient to position the head 54 in the area defined by the surface 50 when the driver assembly is in its first position.

After the implant 11 has been installed into a prepared bone site by rotating the implant 11 through operative engagement between the implant mount 10 and the driver assembly, the housing 14 is moved upwardly relative to the implant mount 10 to its second or superior position as shown in FIG. 5 with the retaining ring 13 positioned in the positioning recess 26. In this position, the hexagonal end 49 is disengaged from the hexagonal surface 24 of the mount 10, and the head 54 of the screw removal insert 16 is engaged with the internal hexagonal surface 51 of the member 15. Thus, in this position, the drive assembly and the implant mount 10 are operatively disengaged from one another and the drive assembly is operatively engaged with the screw removal insert 16 and thus the clamp screw 12. By reversing rotation of the housing 14 with the hand piece, the clamp screw 12 is removed from the implant mount 10. The entire implant mount 10, the clamp screw 12 and the driver assembly can then be removed from the patient's mouth. If desired, a counter-torque tool or member 27 (FIGS. 6 in 14) can be inserted into one of the counter-torque openings 29 in the mount 10 to prevent any reverse rotation during removal of the clamp screw 12. During removal and in fact during the entire installation process, the mount 10 and the clamp screw 12 are captured within the driver assembly via the split ring connector 13.

In its broadest aspect, the method of the present invention is a method for installing a dental implant and removing an implant mount and clamp screw with a single tool. More specifically, the method of the present invention includes providing a driver assembly which is selectively connectable for rotating either the implant mount or the clamp screw, selectively connecting the driver assembly to the implant mount for installation of the implant, subsequently selectively connecting the driver assembly to the clamp screw to withdraw the clamp screw and then removing the driver assembly, clamp screw and implant mount from the patient's mouth.

Although the description of the preferred embodiment has been quite specific, it is contemplated that various modifications could be made without deviating from the spirit of the present invention. For example, the implant mount of the preferred embodiment shows an internal hexagonal surface for connection with an external hexagonal surface of the implant. These, of course, couldn't be reversed. Further, the connection between the implant mount and the implant could be something other than a hex connection. Similarly, the connections between the surfaces 49 and 24, the connections between the head 54 and the surface 51 and the connection between the portion 52 of the insert 16 and the opening 35 of the head 32 could be configured other than hexagonal and could comprise other connecting means. In accordance with the present invention, however, the driver assembly must include some element, elements or means which enable the driver assembly to be selectively connectable to either the implant mount or to the clamp screw.

Further, it is contemplated that the present invention could include means other than the split ring 13 for connecting the driver assembly to the implant mount and for defining the first and second positions of the driver assembly relative to the amount.

I claim:

1. A driver assembly for use with a dental implant assembly comprised of a dental implant, an implant mount and a clamp screw, said driver assembly comprising:
   a drive element;
   a first member being selectively connectable with said implant mount and said drive element for rotation with said implant mount and said drive element;
   a second member being selectively connectable to said clamp screw and said drive element for rotation with said clamp screw and said drive element; and
   said drive element being moveable between an implant installation position in which said first member is connected with said implant mount and said drive element for rotation therewith and said second member is disconnected from one of said clamp screw and said drive element and a screw removal position in which said second member is connected with said clamp screw and said drive element for rotation therewith and said first member is disconnected from one of said implant mount and said drive element.

2. The driver assembly of claim 1 wherein one of said first and second members is fixed relative to said drive element and the other of said first and second members is moveable relative to said drive element.

3. The driver assembly of claim 2 wherein said first member is a drive member fixed relative to said drive element and said second member is a screw removal member moveable relative to said drive element.

4. The driver assembly of claim 1 wherein said drive element includes a sleeve member having an interior surface positionable over an external portion of said implant mount.

5. The driver assembly of claim 4 including a position locating member between said interior surface and said external portion.

6. The driver assembly of claim 1 wherein said drive element includes an end connectable to a dental hand piece.

7. An implant assembly usable with the driver assembly of claim 1 including a dental implant, an implant mount and a clamp screw.

8. A driver assembly for use with a dental implant assembly comprised of a dental implant, an implant mount and a clamp screw, said driver assembly comprising:
   a drive element;
   a first member selectively being connectable with said implant mount and said drive element for rotation with said implant mount and said drive element;
   a second member being selectively connectable to said clamp screw drive element for rotation with said clamp screw drive element wherein said first member is a drive member fixed relative to said drive element and said second member is a screw removal member moveable relative to said drive element and said drive element being moveable between an implant installation position in which said first member is connected with said implant mount and said drive element for rotation therewith and said second member is disconnected from one of said clamp screw and said drive element and a screw removal position in which said second member is connected with said clamp screw and said drive element for rotation therewith and said first member is disconnected from one of said implant mount and said drive element and wherein said drive member and said screw removal member include first and second engagement surfaces, respectively, and wherein said drive member and said screw removal member are movable relative to one another between an engaged position in which said first and second engagement surfaces are engaged with one another and a disengaged position in which said first and second engagement surfaces are disengaged from one another.

9. The driver assembly of claim 8 wherein one of said first and second engagement surfaces is a male hexagonal surface and the other is a female hexagonal surface.

10. The driver assembly of claim 9 wherein said first engagement surface is a female hexagonal surface and said second engagement surface is a male hexagonal surface.

11. A driver assembly for use with a dental implant assembly comprised of a dental implant, an implant mount and a clamp screw, said driver assembly comprising:

a drive element including a sleeve member having an interior surface positionable over an external portion of said implant mount;

a position locating member comprising a snap ring between said interior surface and said external position;

a first member selectively being connectable with said implant mount and said drive element for rotation with said implant mount and said drive element;

a second member being selectively connectable to said clamp screw drive element for rotation with said clamp screw drive element and said drive element being moveable between an implant installation position in which said first member is connected with said implant mount and said drive element for rotation therewith and said second member is disconnected from one of said clamp screw and said drive element and a screw removal position in which said second member is connected with said clamp screw and said drive element for rotation therewith and said first member is disconnected from one of said implant mount and said drive element.

12. An implant assembly usable with a drive assembly having a drive element with a drive member positioning sleeve comprising a first positioning member, a first drive surface and a second drive surface, said implant assembly comprising:

a dental implant;

an implant mount having an implant mount drive surface;

a clamp screw having a clamp screw drive surface connecting said dental implant and said implant mount; and said implant mount having an implant mount positioning sleeve, said implant mount sleeve having a second positioning member engageable with said first positioning member, said implant mount sleeve further being moveable relative to said drive member sleeve between a first position in which said first drive surface is engaged for rotation with said implant mount drive surface and said second drive surface is disengaged from said clamp screw drive surface and a second position in which said first drive surface is disengaged from said implant mount drive surface and said second drive surface is engaged for rotation with said clamp screw drive surface.

13. The implant assembly of claim 12 wherein one of said first and second positioning members includes a pair of positioning grooves and the other of said first and second positioning members includes a protruding portion for seating in said grooves.

14. The implant assembly of claim 13 wherein said second positioning member includes a pair of positioning grooves.

15. The implant assembly of claim 12 wherein said implant mount further includes a non drive surface adjacent to said second drive surface.

16. The implant assembly of claim 15 wherein said second drive surface includes a diametrical dimension and wherein said non drive surface includes a diametrical dimension greater than the diametrical dimension of said second drive surface.

17. A dental implant assembly comprising:

a dental implant having a longitudinal axis;

an implant mount connectable to said dental implant, said implant mount including a proximal end, a distal end and a peripheral edge portion positioned between said proximal and distal ends, said peripheral edge portion having at least one counter-torque opening in said peripheral edge, said counter-torque opening extending substantially radially relative to said longitudinal axis;

a clamp screw connecting said dental implant and said implant mount; and said implant mount including an implant drive portion positioned on the proximal end side of said peripheral edge portion.

18. The dental implant assembly of claim 17 wherein said at least one counter-torque opening tapers inwardly from said peripheral edge toward said longitudinal axis.

19. The dental implant assembly of claim 17 in combination with a counter-torque tool having an end insertable into said at least one counter-torque opening.

20. A method of installing a dental implant and removing an implant mount and clamp screw comprising the steps of:

providing a driver assembly having first and second drive members selectively connectable to said implant mount and said clamp screw, respectively, for separately rotating said implant mount and said clamp screw;

selectively connecting said first drive member to said implant mount and rotating said implant mount to install said implant in a patient's mouth;

disconnecting the said first drive member from said implant mount, selectively connecting said second drive member to said clamp screw and rotating said clamp screw to remove clamp screw; and removing said driver assembly, said clamp screw and said implant mount from the patient's mouth.

21. The method of claim 20 wherein said implant is installed and said implant mount is installed and clamp screw are removed with a single tool.

22. A dental implant and driver assembly comprising:

a dental implant;

an implant mount having an implant mount drive surface;

a clamp screw having a clamp screw drive surface, said clamp screw connecting said dental implant and said implant mount;

a drive element having a first drive surface selectively connectable with said implant mount drive surface and a second drive surface selectively connectable with said clamp screw drive surface;

said implant mount and drive element being selectively moveable relative to one another between an implant installation position in which said first drive surface is connected with said implant mount drive surface for rotation therewith and said second drive surface is disconnected from said clamp screw drive surface and a screw removal position in which said first drive surface and said implant mount drive surface are disconnected and second drive surface is connected with said clamp screw drive surface for rotation therewith.

23. The dental implant and driver assembly of claim 22 wherein said drive element includes a flat sleeve portion having an interior surface portion and said implant mount includes a second sleeve portion having an exterior surface portion, one of said exterior and interior surface portions having a first positioning member and the other of said exterior and interior surface portions having a pair of second positioning members.

24. The dental implant and driver assembly of claim 23 wherein said first positioning member comprises a protrusion from said one of said exterior and interior surfaces and said pair of second positioning members comprise recesses in said other of said exterior and interior surfaces.

* * * * *